United States Patent
Roberts et al.

(10) Patent No.: US 7,090,660 B2
(45) Date of Patent: Aug. 15, 2006

(54) PATIENT MEDICAL TUBING AND CATHETER ANCHOR AND SUPPORT

(75) Inventors: Jerry H. Roberts, Okemos, MI (US); Zane D. Myers, Woodinville, WA (US)

(73) Assignee: Tri-State Hospital Supply Corporation, Howell, MI (US)

( * ) Notice: Subject to any disclaimer, the term of this patent is extended or adjusted under 35 U.S.C. 154(b) by 101 days.

(21) Appl. No.: 10/795,905

(22) Filed: Mar. 8, 2004

(65) Prior Publication Data
US 2005/0197628 A1    Sep. 8, 2005

(51) Int. Cl.
*A61M 5/32* (2006.01)
(52) U.S. Cl. ..................................... 604/174
(58) Field of Classification Search ............... 604/174, 604/179, 180; 128/DIG. 26
See application file for complete search history.

(56) References Cited

U.S. PATENT DOCUMENTS

| | | | | | |
|---|---|---|---|---|---|
| 3,826,254 | A | * | 7/1974 | Mellor | 604/180 |
| 3,834,380 | A | * | 9/1974 | Boyd | 604/180 |
| 4,059,105 | A | * | 11/1977 | Cutruzzula et al. | 604/180 |
| 4,324,236 | A | * | 4/1982 | Gordon et al. | 604/272 |
| 5,147,322 | A | * | 9/1992 | Bowen et al. | 604/180 |
| 5,232,453 | A | * | 8/1993 | Plass et al. | 604/180 |
| 5,372,589 | A | * | 12/1994 | Davis | 604/180 |
| 5,685,859 | A | * | 11/1997 | Kornerup | 604/180 |
| 6,132,398 | A | * | 10/2000 | Bierman | 604/174 |
| 6,689,104 | B1 | * | 2/2004 | Bierman | 604/174 |

* cited by examiner

*Primary Examiner*—Sharon Kennedy
(74) *Attorney, Agent, or Firm*—Fildes & Outland, P.C.

(57) ABSTRACT

A patient medical tubing and catheter anchor and support for permanently, securely anchoring and supporting medical tubing to a patient's body including a longitudinally extending conformable base having a non-adhesive upper surface and a lower surface including a medical grade adhesive thereon. An attachment member is connected to the upper surface of the base to provide a supporting surface for receiving and supporting the tubing. The attachment member includes a center portion and at least one longitudinally extending locking strip extending from one end of the center portion and at least one other longitudinally extending locking strip extending from the other end of the center portion. The locking strips are foldable over the center portion to encapsulate a portion of the tubing between the upper surface of the locking strips and the upper surface of the center portion.

14 Claims, 2 Drawing Sheets

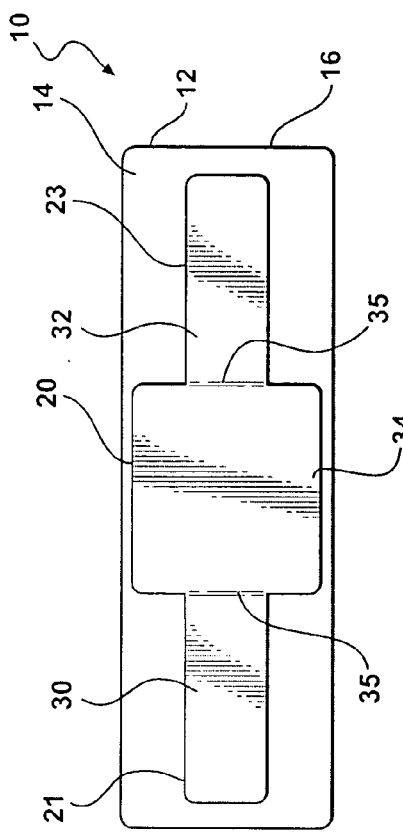
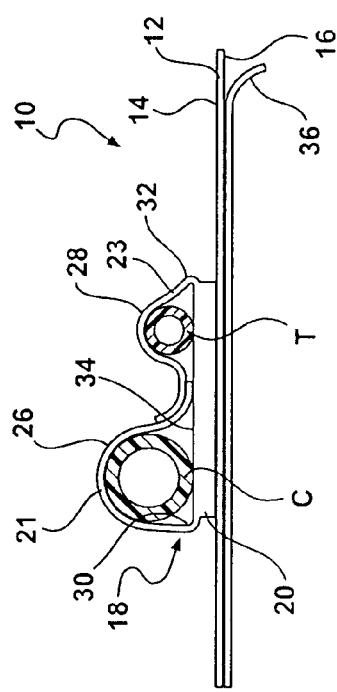
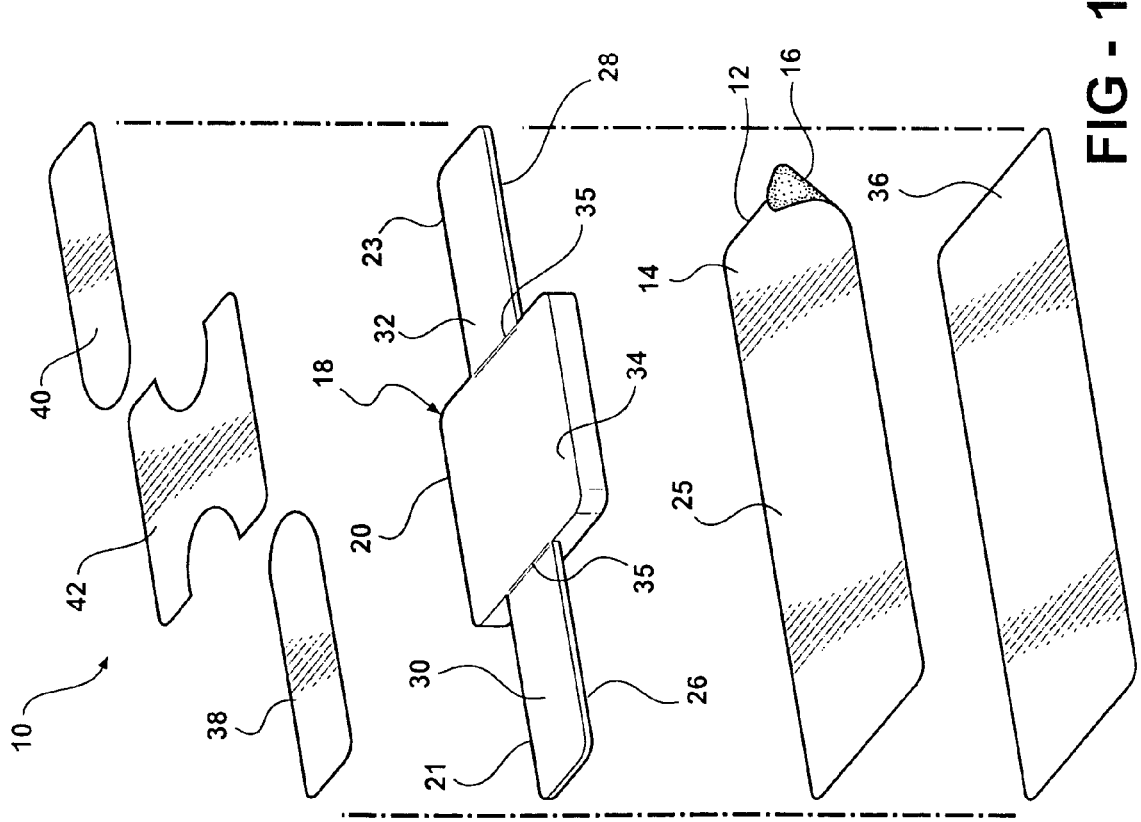

PATIENT MEDICAL TUBING AND CATHETER ANCHOR AND SUPPORT

TECHNICAL FIELD

This invention relates to patient medical tubing securement devices and, more particularly, to medical tubing and catheter anchors for permanently, securely anchoring and supporting percutaneous catheters and/or medical tubing to a patient's skin.

BACKGROUND OF THE INVENTION

Certain medical treatments require the use of percutaneously inserted catheters to direct fluids, such as parenteral liquid or medication directly into a patient's blood stream. After a catheter is percutaneously inserted into a patient at a desired location, the catheter is commonly anchored to the patient by a health care provider, such as, a nurse or a doctor. A common method of anchoring a catheter or medical tubing to a patient's skin includes applying surgical tape over an exposed portion of the catheter or tubing and the patient's skin, or forming a safety loop in tubing, connected to the catheter, and taping the looped tubing to the skin of the patient.

Such taping of a catheter and/or medical tubing to a patient is often ineffective to permanently, securely anchor and support the catheter and/or medical tubing to a patient's skin. Also, the taped down tubing is in direct contact with the patient's skin, which is often reported as being uncomfortable.

Other known anchor devices releasably secure a catheter and/or medical tubing to a patient and these too are often ineffective to permanently, securely anchor and support the catheter and/or medical tubing to a patient's skin.

SUMMARY OF THE INVENTION

The present invention provides an anchor and support for effectively, permanently anchoring and supporting a catheter and/or its associated medical tubing about a patient's body.

According to the invention, the anchor includes a longitudinally extending conformable base formed of woven or nonwoven fabric having a non-adhesive upper surface and a lower surface including a medical grade adhesive thereon for attachment to the skin of a patient's body. An attachment member, formed of a fabric, light weight cellular material or similar, is connected to the upper surface of the base to provide a supporting surface for receiving and supporting a catheter and/or medical tubing. The attachment member includes a center portion and at least one longitudinally extending locking strip extending from one end of the center portion and at least one other longitudinally extending locking strip extending from the other end of the center portion. Each locking strip has non-adhesive lower surfaces and upper surfaces with a permanent adhesive thereon adapted to engage and permanently adhere to a catheter and/or associated medical tubing.

In a preferred embodiment, the upper surface of the center portion may have an adhesive thereon for initially attaching a catheter and/or medical tubing, before the locking strips are folded toward one another, over the center portion, to encapsulate a portion of the catheter and/or medical tubing and provide a permanent attachment.

In a preferred embodiment, perforations may be provided between the locking strips and the center portion operative to tear the locking strips from the center portion.

For storage and shipping purposes, the adhesive surfaces of the anchor may be covered with removable release layers, which act as covers for the adhesive surfaces of the anchor to prevent the loss of adhesion and unintentional sticking.

After the removable release layers are removed from the anchor, the anchor may be applied to the patient's skin proximate a catheter and/or medical tubing. The catheter is then rested on the upper surface of the center portion and the locking strips are subsequently folded over the catheter and the center portion to retain the catheter between the center portion and the locking strips. After a period of time, when the catheter or its associated tubing needs to be removed, the locking strips may be unattached from the center portion, by tearing the strips from the center portion along the perforations, to allow the catheter to be removed.

These and other features and advantages of the invention will be more fully understood from the following detailed description of the invention taken together with the accompanying drawings.

BRIEF DESCRIPTION OF THE DRAWINGS

In the drawings:

FIG. 1 is an exploded perspective view of a patient medical tubing and catheter anchor and support for securing and anchoring a catheter and medical tubing to a person's skin constructed in accordance with the present invention;

FIG. 2 is a plan view of the anchor of FIG. 1;

FIG. 5 is a schematic side view of the anchor of FIG. 1 in an operative disposition wherein the anchor is retaining a catheter and tubing.

DETAILED DESCRIPTION OF THE INVENTION

Figure 3:
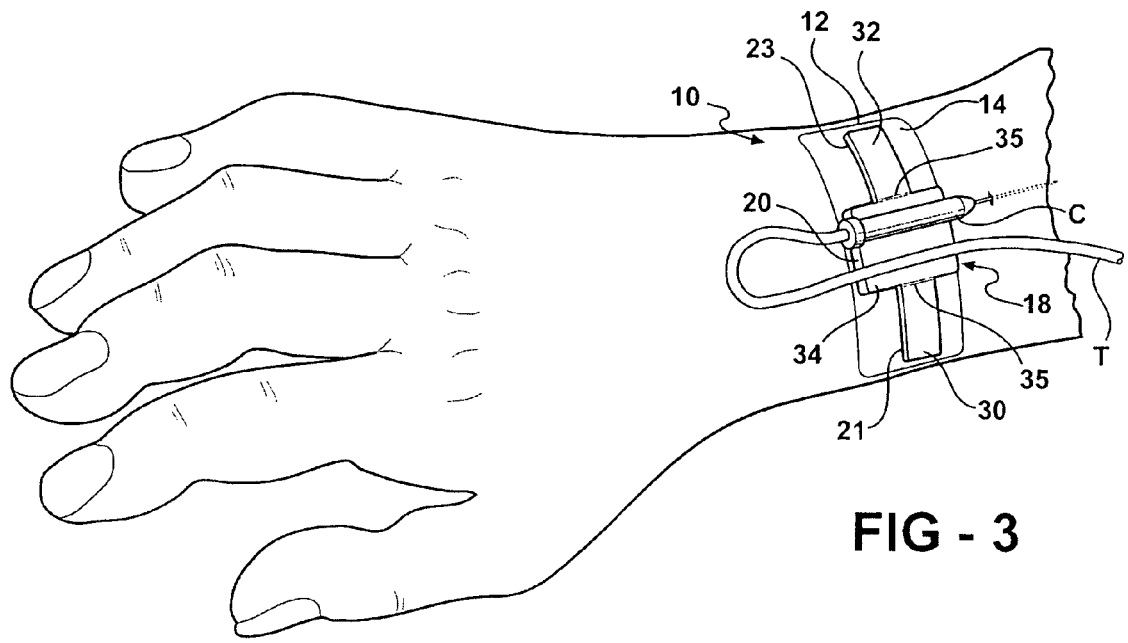
FIG. 3 is an environmental view illustrating the anchor of FIG. 1 adhered onto a person's hand with a catheter and tubing positioned thereon.

Referring now to the drawings in detail, numeral 10 generally indicates an exemplary embodiment of a patient medical tubing and catheter anchor and support. As is hereinafter more fully described, anchor 10 permanently, securely anchors and supports a catheter and/or medical tubing on a patient's skin, avoids the problems inherent in taping, and allows for easy maintenance of a patient catheter.

Referring to FIGS. 1 and 2 of the drawings, the anchor 10 includes a conformable base 12 including a layer formed of flexible woven or nonwoven fabric or other suitable material. The base 12 extends longitudinally and has a non-adhesive upper surface 14 and a lower surface 16 including a medical grade adhesive adapted for attachment to the skin surface of a patient's body. An attachment member 18 connected to the upper surface 14 of the base 12 includes a center portion 20 and at least one longitudinally extending locking strip 21 extending from an end 22 of the center portion and at least one longitudinally extending locking strip 23 extending from an other end 24 of the center portion. It should be understood that only the center portion 20 of the attachment member 18 is adhesively attached to a midportion 25 of the upper surface 14 of the base 12 so that the locking strips 21, 23 are free to be folded toward one another over the center portion 20.

Each of the locking strips 21, 23 respectively have non-adhesive lower surfaces 26, 28 and upper surfaces 30, 32 with a permanent adhesive thereon adapted to engage and permanently adhere to a catheter and/or medical tubing and an upper surface 34 of the center portion 20.

The center portion 20 may be formed of a fabric, light weight cellular material or similar conformable material, to act as a cushioning pad adapted to support and space a catheter and/or medical tubing a distance from a patient's skin.

In a preferred embodiment, the locking strips 21, 23 include perforations 35 adjacent the ends 22, 24 of the center portion 20 for tearing the strips from the center portion.

In a preferred embodiment, the upper surface 34 of the center portion 20 has an adhesive thereon adapted to adhere to a catheter and/or medical tubing and the upper surfaces 30, 32 of the locking strips 21, 23. Alternatively, the upper surface 34 of the center portion 20 may have a non-adherent surface adapted to adhere to the adhesive upper surfaces 30, 32 of the locking strips 21, 23 when the strips are folded toward one another, over the center portion, in an overlapping relation.

For storage and shipping purposes, a removable non-adhesive release layer 36 of known construction may cover the adhesive lower surface 16 of the base 12 to prevent the base from inadvertently sticking to an object or loosing its adhesive qualities. Additional removable release layers 38, 40 may cover the adhesive upper surfaces 30, 32 of the locking strips 21, 23 to prevent the locking strips from sticking or loosing their adhesive quality. An additional removable release layer 42 may cover the adhesive upper surface 34 of the center portion 20 to protect the adhesive and prevent the center portion from sticking to an object before a desired application.

Figure 4:
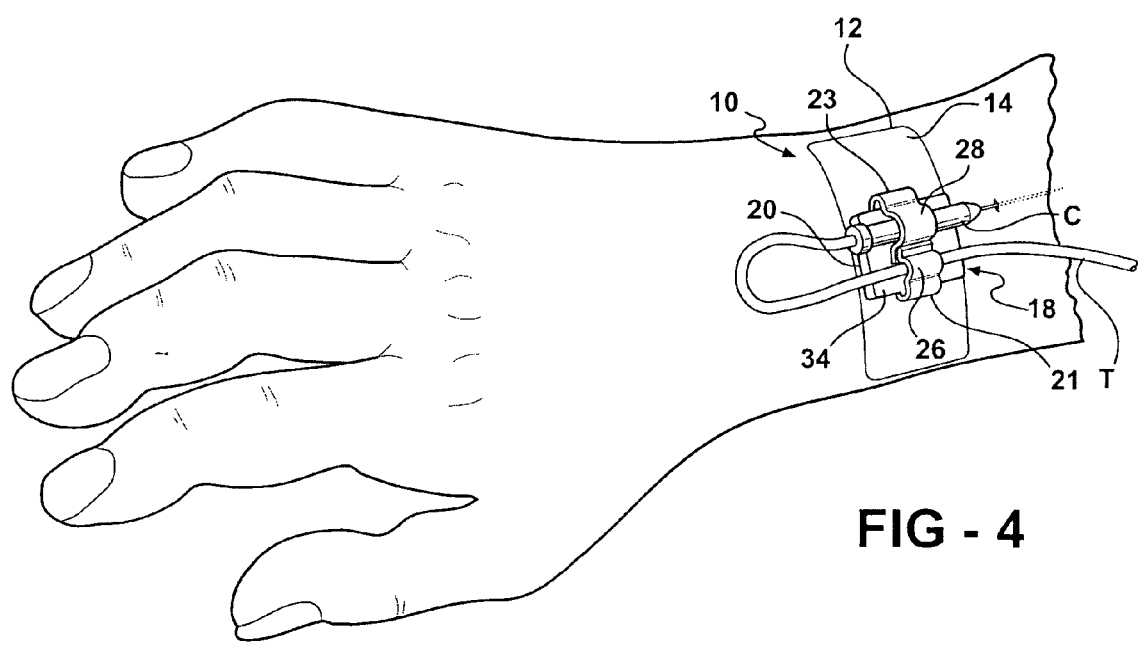
FIG. 4 is an other environmental view similar to FIG. 3 wherein the anchor is retaining the catheter and tubing.

Referring to FIGS. 3–5, in operation, a health care provider, such as a nurse or the like, removes the release layer 36 from the lower surface 16 of the base 12 and attaches the lower surface 16 to a patient's skin, proximate a catheter C. The catheter C is then positioned over the center portion 20 of the attachment member 18, as shown in FIG. 3. When adhesive is present on the upper surface 34 of the center portion 20, the adhesive initially retains the catheter C on the center portion 20. The release layers 38, 40 are then removed from the locking strips 21, 23. Locking strip 21 is then folded over the center portion 20, toward locking strip 23, so the upper surface 30 of locking strip 21 engages the catheter C. This retains the catheter C between the locking strip 21 and the center portion 20 of the anchor 10. If desired, locking strip 23 may be folded over the center portion 20, toward locking strip 22, so that the adhesive upper surface 32 of the locking strip engages the lower surface 26 of the locking strip 21 to improve the anchoring effect of the anchor on the catheter C, as shown in FIGS. 4–5. While the catheter C is retained by the anchor 10, the attachment member 18 spaces the catheter a distance from the patient's skin and acts as a cushioning pad between the patient's skin to improve patient comfort.

If desired, a combination of catheters and medical tubing may be positioned on the center portion 20, to allow a single anchor 10 to retain multiple catheters or tubes. Once the combination of catheters and medical tubing are positioned on the center portion 20, the locking strips 21, 23 are folded toward one another, over the center portion 20, to retain the combination of catheters and tubing.

After a period of time, when the catheter C or tubing T requires replacement or removal, the catheter C or tubing T may be removed by tearing the locking strips 21, 23 along the perforations 35 extending adjacent the ends 22, 24 of the center portion 20. When the catheter C is no longer needed, the anchor 10 and catheter can be removed simultaneously by detaching the base 12 from the patient's skin and pulling the catheter C from the patient.

It should be understood that the anchor 10 may be attached to a patient before a catheter is inserted, to provide an immediate anchor for the catheter after insertion.

It should also be understood that the above described anchor 10 is not limited to use with IV catheters. The present invention may be used in conjunction with other types of medical lines such as tubes for fluid communication, electrical wires, CVCs, PICCs, Foley catheters, hemodialysis catheters, surgical drainage tubes, feeding tubes, chest tubes, nasogastric tubes, scopes, as well as with electrical wires or cables connected to external or implanted electronic devices or sensors.

Although the invention has been described by reference to certain specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A patient medical tubing anchor and support adapted for use on a patient comprising:
    a conformable generally laminar base layer member extending longitudinally having a lower surface adapted for adhesion to a person's skin and a non-adhesive upper surface; and
    a generally laminar attachment layer member connected to the upper surface of the base having a center portion defining a cushioning pad and at least one integral longitudinally extending locking strip extending from one end of the center portion and at least one other integral longitudinally extending locking strip extending from the other end of the center portion;
    the center portion having an upper surface operative to support medical tubing;
    the locking strips having a non-adhesive lower surface and a permanent adhesive upper surface;
    the locking strips being foldable over the center portion to encapsulate a portion of said medical tubing between the upper surface of the locking strips and the upper surface of the center portion;
    wherein said medical tubing anchor and support is disposed between patient medical tubing and skin to anchor said tubing without affecting the parallel relationship of said tubing to the skin.

2. A patient medical tubing anchor and support as in claim 1 wherein said center portion is a cushioning pad.

3. A patient medical tubing anchor as in claim 2 wherein said cushioning pad is a light weight cellular material.

4. A patient medical tubing anchor and support as in claim 1 wherein the base is one of a woven and nonwoven strip.

5. A patient medical tubing anchor and support as in claim 1 further comprising a removable non-adhesive release layer on the adhesive upper surfaces of the locking strips.

6. A patient medical tubing anchor and support as in claim 1 further comprising a removable non-adhesive release layer attached to the adhesive lower surface of the base.

7. A patient medical tubing anchor and support as in claim 1 further comprising adhesive on the upper surface of the attachment member operative to retain medical tubing.

8. A patient medical tubing anchor and support as in claim 7 further comprising a removable non-adhesive release layer on the upper surface of the center portion.

9. A patient medical tubing anchor and support as in claim 1 wherein the length of the center portion is greater than the length of the locking strips.

10. A patient medical tubing anchor and support as in claim 1 further comprising perforations between the locking strips and the center portion operative to tear the locking strips from the center portion.

11. A method of anchoring and supporting medical tubing on a person's skin, the steps comprising:

provining a medical tubing anchor comprising a conformable generally laminar base member including a layer extending longitudinally having a lower surface adapted for adhesion to a person's skin and a non-adhesive upper surface, a generally laminar attachment layer member connected to the upper surface of the base having a center portion defining a cushioning pad and at least one integral longitudinally extending locking strip extending from one end of the center portion and at least one other integral longitudinally extending locking strip extending from the other end of the center portion, the center portion having an upper surface operative to support medical tubing, the locking strips having a non-adhesive lower surface and a permanent adhesive upper surface, and the locking strips being foldable over the center portion to encapsulate a portion of said medical tubing between the upper surface of the locking strips and the upper surface of the center portion, wherein said medical tubing anchor and support is disposed between patient medical tubing and skin to anchor said tubing without affecting the parallel relationship of said tubing to the skin.

12. The method as in claim 11 further including the step of attaching the base of the anchor to a person's skin.

13. The method as in claim 12 further including the step of positioning a portion of the medical tubing over the center portion.

14. The method as in claim 13 further including the step of folding the locking strips in an overlapping fashion to encapsulate a portion of the medical tubing between the upper surface of the locking strips and the upper surface of the center portion.

* * * * *